United States Patent [19]

Gallop et al.

[11] Patent Number: 5,525,734
[45] Date of Patent: Jun. 11, 1996

[54] METHODS FOR SYNTHESIZING DIVERSE COLLECTIONS OF PYRROLIDINE COMPOUNDS

[75] Inventors: Mark A. Gallop, Los Altos; Martin A. Murphy, Mt. View, both of Calif.

[73] Assignee: Affymax Technologies N.V., Curaco, Netherlands

[21] Appl. No.: 264,136

[22] Filed: Jun. 22, 1994

[51] Int. Cl.[6] .................. C07D 207/00; C07D 209/00
[52] U.S. Cl. .................. 548/453; 548/400; 548/406; 548/517; 548/518; 548/532; 548/533; 548/536; 548/537; 548/541; 548/560; 548/565; 548/566; 548/570; 548/577; 435/7.92; 436/518
[58] Field of Search .................. 548/400, 532, 548/533, 536, 537

[56] References Cited

U.S. PATENT DOCUMENTS 5,143,854  9/1992  Pirrung et al. .

FOREIGN PATENT DOCUMENTS

WO91/05058  4/1991  WIPO .
WO91/17271  11/1991  WIPO .
WO91/19818  12/1991  WIPO .
WO92/02536  2/1992  WIPO .
WO93/06121  4/1993  WIPO .
WO93/08278  4/1993  WIPO .

OTHER PUBLICATIONS

Furka, et al.; Int. J. Peptide Protein Res., 37, pp. 487–493 (1991).
Ellman; Archives of Biochemistry and Biophysics, 82, pp. 70–77 (1959).
Cheung, et al.; Biochimica & Biopbysica Acta, 293, pp. 451–463 (1973).
Bull, et al.; J. of Biological Chemistry, 260, pp. 2952–2962 (1985).
Tsuge, et al.; Org. Chem., 53, pp. 1384–1391 (1988).
Petrillo, Jr., et al.; Med. Res. Rev., 2, pp. 1–41 (1982).
Gallop, et al., J. Med. Chem., 37(9):1233–1251 (29 Apr. 1994).
Gordon, et al., J. Med. Chem., 37(10):1385–1401 (1994).
Williams, et al., J. Org. Chem., 57(24):6527–6532 (1992).
Grigg, et al., Tetrahedron, 48(47)10431–10442 (1992).
Williams et al., 1992, J. Org. Chem. 57:6527–6532; Asymmetric [1,3]-Dipolar Cycloaddition Reactions: Synthesis of Highly Substituted Proline Derivatives.
Allway et al., "Chiral Co(II) and MN(II) Catalysts for the 1,3-Dipolar Cycloaddition Reactions of Azomethine Ylides Derived from Arylidene Imines of Glycine," Tetrahedron Letters, vol. 32, No. 41, pp. 5817–5820 (1991).
Aly et al., "X=Y–ZH Compounds as Potential 1,3-Dipoles. Part 41.[1] Azomethine Ylide Formation from the Reactions of α–Amino Acids and Esters with Alloxan (Strecker Degradation) and with 1-Phenyl-3-methylpyrazoline-4,5-dione," Tetrahedron, vol. 50, No. 3, pp. 895–906 (1994).

Amornraksa et al., "X=Y–ZH Compounds as Potential 1,3-Dipoles, Part 24.[1,2] Preparation and Thermal Fragmentation of Imidazolidines. Influence of Metal Salts on Pyrrolidine Versus Imidazolidine Formation," Tetrahedron, vol. 45, No. 14, pp. 4649–4668 (1989).
Ardill et al., "X=Y–ZH Systems as Potential 1,3-Dipoles. Part 19.[1] Intramolecular Cycloadditions of Non–Stabilized Azomethine Ylides Generated Via The Decarboxylative Route From α–Amino Acids," Tetrahedron, vol. 44, No. 15, pp. 4953–4966 (1988).
Ardill et al., "Iminium Ion Route to Azomethine Ylides from Primary and Secondary Amines," J. Chem. Soc. Chem. Commun., pp. 602–604 (1986).
Armstrong et al., "X=Y–ZH Systems as Potential 1,3-Dipoles—5[1] Intramolecular Cycloadditions of Imines of α–Amino Acid Esters," Tetrahedron, vol. 41, No. 17, pp. 3547–3558 (1985).
Barr et al, "Metal Ion Catalyzed Asymmetric 1,3-Dipolar Cycloaddition Reactions of Imines of α–Amino Esters," Tetrahedron Letters, vol. 31, No. 45, pp. 6569–6572 (1990).
Barr et al., "X=Y–ZH Systems as Potential 1,3-Dipoles. Part 15[1]. Amine Generated Azaallyl Anions Versus Metallo–1,3–Dipoles in Cycloadditions of α–Amino Acid Esters. Facile Regio–and Stereo–Specific Formation of Pyrrolidines," Tetrahedron, vol. 44, No. 2, pp. 557–570 (1988).
Barr et al., "Ti(IV) Mediated Transesterification and Regio- and Stereo–Specific Cycloaddition of Imines of α–Amino Esters. Reversal of Normal Regiochemistry," Tetrahedron Letters, vol. 30, No. 35, pp. 4727–4730 (1989).
Boger et al., "Total Synthesis of (+)-Piperazinomycin," J. Am. Chem. Soc., vol. 115, No. 24, pp. 11426–11433 (1993).
Cull et al., "Screening for Receptor Ligands Using Large Libraries of Peptides Linked to the C Terminus of the lac Repressor," Proc. Natl. Acad. Sci., USA, vol. 89, pp. 1865–1869 (1992).
Cwirla et al., "Peptides on Phage: A Vast Library of Peptides for Identifying Ligands," Proc. Natl. Acad. Sci., USA, vol. 87, pp. 6378–6382 (1990).
Devlin et al., "Random Peptide Libraries: A Source of Specific Protein Binding Molecules," Science, vol. 249, pp. 404–406 (1990).
Dorrity et al., "X=Y–ZH Systems as Potential 1,3-Dipoles. Part 18.[1] Cycloaddition of 4π-Sulphinylaminomethamide Species Generated from α–Amino Acids and α–Amino Acid Esters by Sulphonyl Group Transfer.[2] X–Ray Crystal Structure of 4-Iso-Propyl-7-Methyl-2-Thia-6,8-Dioxo-3,7-Diazobicyclo[3.3.0]Octane S–Oxide," Tetrahedron, vol. 44, No. 15, pp. 4941–4952 (1988).
Grigg et al., "X=Y–ZH Systems As Potential 1,3-Dipoles. Part 14.[1] Bronsted and Lewis Acid Catalysis off Cycloadditions of Arylidene Imines of α–Amino Acid Esters.[2]," Tetrahedron, vol. 43, No. 24, pp. 5887–5898 (1987).

(List continued on next page.)

Primary Examiner—Joseph Paul Brust
Attorney, Agent, or Firm—Burns, Doane, Swecker & Mathis

[57] ABSTRACT

Disclosed are methods for synthesizing very large collections of diverse pyrrolidine compounds on solid supports and synthetic compound libraries comprising pyrrolidine groups prepared by such methods.

5 Claims, 2 Drawing Sheets

OTHER PUBLICATIONS

Grigg et al., "The Decarboxylative Route to Azomethine Ylides. Stereochemistry of 1,3-Dipole Formation," *J. Chem. Soc. Chem. Commun.*, pp. 47–51 (1987).

Grigg et al., "X=Y–ZH Systems As Potential 1,3-Dipoles. Part 38.[1] 1-5-Electrocyclization of Vinyl-and Iminyl-azomethine Ylides. 2-Azaindolizines and Pyrrolo-dihydro-isoquinolines," *Tetrahedron*, vol. 48, No. 47, pp. 10423–10430 (1992).

Grigg et al., "The Mechanism of the Racemization of α–Amino Acids in the Presence of Aldehydes," *Tetrahedron Letters*, vol. 24, No. 41, pp. 4457–4460 (1983).

Grigg et al., "X=Y–ZH Systems As Potential 1,3-Dipoles. The Stereochemistry and Regiochemistry of Cycloaddition Reactions of Imines of α-Amino–Acid Esters," *Tetrahedron Letters*, vol. 21, pp. 2461–2464 (1980).

Grigg, "Prototropic Routes to 1,3– and 1,5–Dipoles, and 1,2–Ylides: Applications to the Synthesis of Heterocyclic Compounds," *Chem. Soc. Rev.*, vol. 16, pp. 89–121 (1987).

Grigg et al., "X=Y–ZH Systems As Potential 1,3-Dipoles. Part 21.[1] Activation of the ZH Proton in Imines.[2]," *Tetrahedron*, vol. 45, No. 6, pp. 1723–1746 (1989).

Grigg, et al., "X=Y–ZH Systems As Potential 1,3–Dipoles. Part 40.[1] Chiral Azomethine Ylides From Homochiral Cyclic α–Amino Esters. Unusual Regiospecific Deprotonation of Iminum Ions," *Tetrahedron*, vol. 49, No. 38, pp. 8679–8690 (1993).

Grigg et al., "X=Y–ZH Systems As Potential 1,3–Dipoles. Part 39.[1] Metallo–Azomethine Ylides from Aliphatic Aldimines. Facile Regio– and Stereo–specific Cycloaddition Reactions," *Tetrahedron*, vol. 48, No. 47, pp. 10431–10442 (1992).

Hwang et al., "Specific Receptor Sites for 1–O–Alkyl–2–O–acetyl–sn–glycero–3–phosphocholine (Platelet Activating Factor) on Rabbit Platelet and Guinea Pig Smooth Muscle Membranes," *Biochemistry*, vol. 22, pp. 4756–4763 (1983).

Scott et al., "Searching for Peptide Ligands with an Epitope Library," *Science*, vol. 249, pp. 386–390 (1990).

Tsuge et al., "Recent Advances in Azomethine Ylide Chemistry," *Advances in Heterocyclic Chemistry*, vol. 45, pp. 231–349, Academic Press, Inc. (1989).

Beebe et al., "Polymer–Supported Synthesis of 2,5–Disubstituted Tetrahydrofurans," *J. am. Chem. Soc.*, 114:10061–10062 (1992).

METHODS FOR SYNTHESIZING DIVERSE COLLECTIONS OF PYRROLIDINE COMPOUNDS

BACKGROUND OF THE INVENTION

1. Field of the Invention

This invention is directed to methods for synthesizing very large collections of diverse pyrrolidine compounds on solid supports. This invention is further directed to methods for identifying and isolating pyrrolidine compounds with useful and diverse activities from such collections. This invention is still further directed to the incorporation of identification tags in such collections to facilitate identification of compounds with desired properties.

2. References

The following publications, patents and patent applications are cited in this application as superscript numbers:

[1] Tsuge, et al., Recent Advances in Azomethine Ylide Chemistry, in "Advances in Heterocyclic Chemistry", Vol. 45, pp. 231–349, Academic Press, Inc. (1989)
[2] Cwirla, et al., Proc. Natl. Acad. Sci., USA, 87:6378–6382 (1990)
[3] Scott & Smith, Science, 249:386–390 (1990)
[4] Devlin, et al., Science, 249:404–406 (1990)
[5] Cull, et al., Proc. Natl. Acad. Sci., USA, 89:1865–1869 (1992)
[6] International Patent Application Publication No. WO 91/17271
[7] International Patent Application Publication No. WO 91/19818
[8] International Patent Application Publication No. WO 93/08278
[9] International Patent Application Publication No. WO 91/05058
[10] International Patent Application Publication No. WO 92/02536
[11] International Patent Application Publication No. WO 93/06121
[12] U.S. patent application Ser. No. 07/946,239
[13] U.S. Pat. No. 5,143,854, issued Sep. 1, 1992
[14] Adrill, et al., Tetrahedron, 44(15):4953–4966 (1988)
[15] Dorrity, et al., Tetrahedron, 44(15):4941–4952 (1988)
[16] Grigg, et al., Tetrahedron, 45(6):1723–1746 (1989)
[17] Grigg, Chem. Soc. Rev., 16:89–121 (1987)
[18] Barr, et al, Tetrahedron Letters, 30(35):4727–4730 (1989)
[19] Allway, et al., Tetrahedron Letters, 32(41):5817–5820 (1991)
[20] Barr, et al., Tetrahedron Letters, 31(45):6569–6572 (1990)
[21] Grigg, et al., Tetrahedron Letters, 21:2461–2464 (1980)
[22] Barr, et al., Tetrahedron, 44(2):557–570 (1988)
[23] Amornraksa, et at., Tetrahedron, 45:(14):4649–4668 (1989)
[24] Armstrong, et al., Tetrahedron, 41:(17):3547–3558 (1985)
[25] Grigg, et al., Tetrahedron, 49(38):8679–8690 (1993)
[26] Grigg, et al., Tetrahedron, 48(47):10431–10442 (1992)
[27] Grigg, et al., Tetrahedron, 43(24):5887–5898 (1987)
[28] Grigg, et al., J. Chem. Soc. Chem. Commun., pp. 47–51 (1987)
[29] Grigg, et al., Tetrahedron, 48(47):10423–10430 (1992)
[30] Grigg, et al., Tetrahedron Letters, 24(41):4457–4460 (1983)
[31] Aly, et al., Tetrahedron, 50(3):895–906 (1994)

All of the above publications, patents and patent applications are herein incorporated by reference in their entirety to the same extent as if each individual publication, patent or patent application was specifically and individually indicated to be incorporated by reference in its entirety.

3. State of the Art

Ligands for macromolecular receptors can be identified by screening diverse collections of compounds, e.g., peptides, produced through either molecular biological or synthetic chemical techniques. For example, recombinant peptide libraries have been generated by inserting degenerate oligonucleotides into genes encoding capsid proteins of filamentous bacteriophage and the DNA-binding protein Lac I.[2-8] These random libraries contain more than $10^9$ different peptides, each fused to a larger protein sequence that is physically linked to the genetic material encoding it. Such libraries are efficiently screened for interaction with a receptor by several rounds of affinity purification, the selected exposition or display vectors being amplified in E. coli and the DNA of individual clones sequenced to reveal the identity of the peptide responsible for receptor binding.[9,10]

Other disclosed methods for screening libraries of compounds for binding properties to a receptor include methods wherein each member of the library is tagged with a unique identifier tag to facilitate identification of compounds having binding properties[11,23] or where the library comprises a plurality of compounds synthesized at specific locations on the surface of a solid substrate wherein the receptor is appropriately labeled to identify binding, e.g., fluorescent or radioactive labels. Correlation of the labelled receptor bound to the substrate with its location on the substrate identifies the binding ligand.[13]

Central to these methods is the screening of a multiplicity of compounds in the library and the ability to identify the structures of the compounds which have a requisite binding affinity for the receptor. Preferably, in order to facilitate synthesis and identification, the compounds in the library are typically formed on solid supports wherein the compound is covalently attached to the support via a cleavable or non-cleavable linking arm. In this regard, the diversity of naturally occurring amino acids permits the generation of extensive peptide libraries on such solid supports without resort to the use of synthetic amino acids which can include derivatives of naturally occurring amino acids. These libraries are then screened to identify "lead compounds" having good binding affinity to the receptor.

Pharmaceutical drug discovery relies heavily on studies of structure-activity relationships wherein the structure of "lead compounds" is typically altered to determine the effect of the alteration on activity. When the lead compound comprises one or more amino acids (e.g., a peptide), alteration of the structure of one or more of the amino acid(s) permits evaluation of the effect of the structural alteration on activity. Thus libraries of compounds derived from a lead compound can be created by including derivatives of the amino acids in the peptides and repeating the screening procedures.

The use of such amino acid derivatives in these libraries has been disclosed in the art.[12,13] Ideally, the amino acid derivative is synthesized in situ on the solid support so that the support can be tagged to identify the synthetic steps employed and/or the derivative incorporated onto the support. However, relatively simple synthetic methods to produce a diverse collection of such derivatives on the supports are often not available.

One particular class of compounds which would be useful for inclusion in screening libraries are pyrrolidine compounds, including proline and derivatives thereof. These compounds form the basis of an important class of compounds having diverse pharmaceutical and chemical properties. Proline, itself, is often included in the structure of peptides having receptor binding activity and derivatives of proline form important pharmaceutical compositions such as Captopril, a commercial anti-hypertensive agent. Similarly, pyrrolidine compounds are the central skeletal feature on numerous alkaloids.[1]

The inclusion of certain proline derivatives into such libraries is well known in the art. However, a simple procedure for the in situ incorporation of a multiplicity of pyrrolidine derivatives on solid supports is not previously known. The ability to synthesize a multiplicity of pyrrolidine derivatives on a solid support or on different solid supports would enhance the structural variation of a library and provide important structure-activity information.

SUMMARY OF THE INVENTION

This invention is directed to general synthetic methods for incorporating a pyrrolidinyl group on a solid support which methods can be employed in conjunction with known stochastic methods for preparing libraries of compounds comprising one or more pyrrolidinyl groups.

Solid supports containing such pyrrolidinyl groups preferably comprise a linking arm which links the solid support to the compound. The linking arm can be either clearable or non-clearable and when clearable, can be used to prepare a library of soluble compounds. The library of compounds on the solid support comprises monomers and sequences of monomers (e.g., oligomers and polymers), the monomers employed with such oligomers and polymers being any member of the set of molecules which can be joined together to form an oligomer or polymer (e.g., amino acids, carbamates, sulfones, sulfoxides, nucleosides, carbohydrates, ureas, phosphonates, lipids, esters, combinations of the same, and the like). In the case of a library of monomers, the compound attached to the solid support is a pyrrolidine compound and, in the case of libraries of oligomers and polymers, at least one of the monomers of the oligomer and polymer is a pyrrolidinyl group.

The library is screened to isolate individual compounds that bind to a receptor or possess some desired property. In a preferred embodiment, each compound in the library is unique.

Accordingly, in one of its method aspects, this invention is directed to a method for synthesizing a pyrrolidinyl group covalently attached to a solid support which method comprises:

(a) selecting a solid support comprising at least one compound covalently attached thereto which compound comprises a moiety selected from the group consisting of a complementary group having at least one site of carbon-carbon unsaturation and an azomethine ylide precursor;

b) converting said moiety to a pyrrolidinyl group.

The solid supports prepared in the methods described above can be used, for example, in creating libraries of compounds in the manner described in International Patent Application Publication No. WO 93/06121 or in the solid supports described in U.S. Pat. No. 5,143,854, to screen said compounds for binding affinity to ligands.

Accordingly, in another of its method aspects, this invention is directed to a method for preparing a synthetic compound library produced by synthesizing on each of a plurality of solid supports a single compound wherein each compound comprises at least one pyrrolidinyl group, which library is synthesized in a process comprising:

a) apportioning the supports comprising a covalently bound azomethine ylide precursor or a covalently bound complementary group comprising at least one site of carbon-carbon unsaturation among a plurality of reaction vessels;

b) exposing the supports in each reaction vessel under conditions wherein the azomethine ylide precursor or the complementary group is converted to a pyrrolidinyl group wherein said pyrrolidinyl group is different for each of the reaction vessels; and c) pooling the supports.

In one embodiment procedures a) through c) are conducted only once whereas in another embodiment procedures a) through c) are repeated up to about 20 times.

If procedure a) through c) are conducted only once, then the resulting library comprises a library of different pyrrolidine compounds covalently attached to the solid support. These pyrrolidine compounds can be either directly attached or linked to the solid support or can be part of a larger molecule already synthesized on the support.

If procedures a) through c) are conducted a multiple number of times, then each of the resulting compounds is an oligomer/polymer.

Preferably, in the methods described above, the azomethine ylide precursor is converted to the pyrrolidinyl group by converting this precursor to an azomethine ylide which is then reacted with a complementary compound having at least one site of carbon-carbon unsaturation so as to form a pyrrolidinyl group. Likewise, the complementary group or moiety having at least one site of carbon-carbon unsaturation is preferably converted to a pyrrolidinyl group by reaction with an azomethine ylide.

In still another of its method aspects, this invention is directed to a method for preparing a synthetic compound library produced by synthesizing on each of a plurality of solid supports a single compound, wherein each compound comprises a pyrrolidinyl group, which library is synthesized in a process comprising:

a) apportioning the supports among a plurality of reaction vessels;

b) exposing the supports in each reaction vessel to a first monomer under conditions wherein the first monomer becomes covalently linked to the support wherein said first monomer is different for each of the reaction vessels;

c) pooling the supports; and d) optionally repeating procedures a) through c) up to about 20 times;

wherein at least one of the monomers employed in procedure b) comprises a moiety selected from the group consisting of a complementary compound having at least one site of carbon-carbon unsaturation and a group convertible to an azomethine ylide precursor which moiety is converted to a pyrrolidinyl group prior to procedure c).

In the case, where the monomer contains a moiety convertible to an azomethine ylide precursor, conversion to the pyrrolidinyl group is achieved by first converting this moiety to an azomethine ylide precursor, then to the azomethine ylide followed by reaction with a complementary compound having at least one site of carbon-carbon unsaturation. As before, conversion of a complementary compound having at least one site of carbon-carbon unsaturation to the pyrrolidinyl group is by reaction with an azomethine ylide.

Moieties convertible to azomethine ylide precursors include aldehyde and ketone moieties as well as primary amines having a methine or methylene hydrogen atom alpha to the amino group. Such moieties are readily convertible to imines having a methine or methylene hydrogen atom alpha to the amino group which, as noted below, are azomethine ylide precursors.

In a preferred embodiment for each of the above described methods, the azomethine ylide precursor is an imine group having a methine or methylene hydrogen atom alpha to the nitrogen atom of the imine group or is convertible to such an imine group which is preferably linked to the solid support through a linking arm.

In a further preferred embodiment for each of the above described methods, the resulting pyrrolidinyl group comprises a secondary amino group in the ring structure which can optionally be employed to further modify the pyrrolidinyl group.

In one of its composition aspects, this invention is directed to a synthetic compound library comprising a plurality of different compounds each compound covalently linked to a solid support wherein each of said compounds comprise at least one pyrrolidinyl group which group is prepared by the method which comprises (a) selecting a solid support comprising at least one compound attached thereto which compound comprises a moiety selected from the group consisting of a complementary group having at least one site of carbon-carbon unsaturation and an azomethine ylide precursor;

(b) converting said moiety to a pyrrolidinyl group.

In one embodiment, each compound of said plurality of different compounds is covalently linked to the same solid support in the manner described in U.S. Pat. No. 5,143,854. In another embodiment, each compound of said plurality of different compounds is covalently linked to a different solid support in the manner described in International Patent Application Publication No. WO 93/06121. Both U.S. Pat. No. 5,143,854 and International Patent Application Publication No. 93/06121 are incorporated herein by reference in their entirety.

In one preferred embodiment, the —NH moiety of the pyrrolidinyl group is used to incorporate this group into a peptide compound wherein the pyrrolidinyl group is located at any point in the peptide sequence. In another preferred embodiment, the NH moiety of the pyrrolidinyl group is modified by acylation, sulfonylation, alkylation and the like to form a variety of pyrrolidinyl derivatives.

In yet another preferred embodiment, the library comprises a plurality of pyrrolidinyl monomers (compounds) which are screened for biological or pharmaceutical activity.

DETAILED DESCRIPTION OF THE INVENTION

This invention is directed to synthetic methods for preparing pyrrolidinyl groups in situ on solid supports and the use of these methods to incorporate pyrrolidinyl groups in large synthetic compound libraries.

Prior to discussing this invention in further detail, the following terms will first be defined:

The term "substrate" or "solid support" refers to a material having a rigid or semi-rigid surface which contain or can be derivatized to contain reactive functionality which covalently links a compound to the surface thereof. Such materials are well known in the art and include, by way of example, silicon dioxide supports containing reactive Si—OH groups, polyacrylamide supports, polystyrene supports, polyethyleneglycol supports, and the like. Such supports will preferably take the form of small beads, pellets, disks, or other conventional forms, although other forms may be used. In some embodiments, at least one surface of the substrate will be substantially flat.

The term "azomethine ylide precursor" refers to any group, substituent or functionality which is convertible to an azomethine ylide. Such precursors are known in the art[1,14-31] and include, by way of example only, aziridines, imines having a methine or methylene hydrogen atom α to the nitrogen atom of the imine, and the like.

The compounds comprising an azomethine ylide precursor can be covalently attached directly to the solid support or can be attached via a linking arm. Linking arms are well known in the art and include, by way of example only, conventional linking arms such as those comprising ester, amide, carbamate, ether, thio ether, urea, amine groups and the like.

The linking arm can be cleavable or non-cleavable. "Cleavable linking arms" refer to linking arms wherein at least one of the covalent bonds of the linking arm which attaches the compound comprising the pyrrolidinyl group to the solid support can be readily broken by specific chemical reactions thereby providing for compounds comprising pyrrolidinyl groups free of the solid support ("soluble compounds"). The chemical reactions employed to break the covalent bond of the linking arm are selected so as to be specific for bond breakage thereby preventing unintended reactions occurring elsewhere on the compound. The cleavable linking arm is selected relative to the synthesis of the compounds to be formed on the solid support so as to prevent premature cleavage of this compound from the solid support as well as not to interfere with any of the procedures employed during compound synthesis on the support.

Figure 2A:
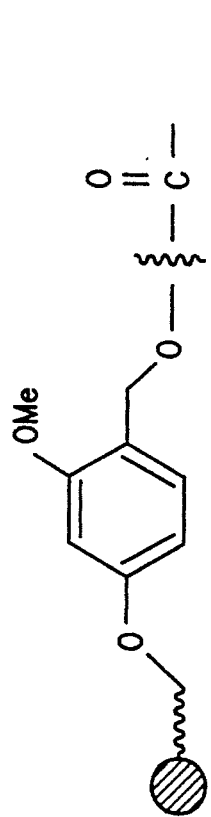
FIGS. 2A–2D illustrates several cleavable linking arms for covalently linking compounds comprising at least one pyrrolidinyl group to the solid support.

Suitable cleavable linking arms are well known in the art and FIGS. 2A–2D illustrates several embodiments of such linking arms. Specifically, FIG. 2A illustrates a cleavable Sasrin resin comprising polystyrene beads and a cleavable linking arm as depicted therein which linking arm is cleaved by strong acidic conditions such as trifluoroacetic acid. Cleavage results in breakage at the vertical line interposed between the oxygen and carbonyl moieties of the ester so as to provide for a compound terminating in a carboxylic acid.

Figure 2B:
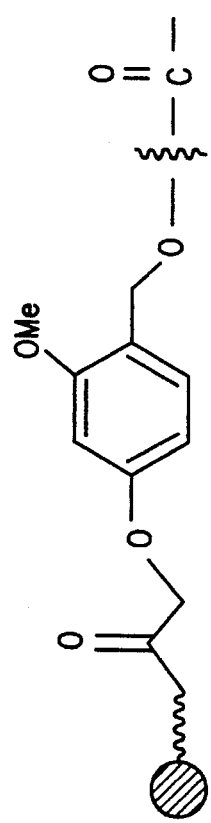
Figure 2C:
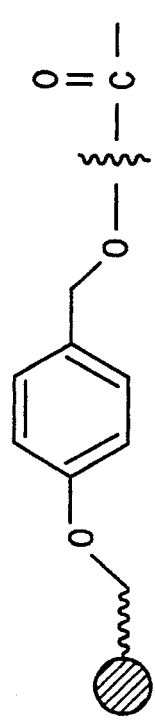

FIGS. 2B and 2C illustrate cleavable TentaGel AC and TentaGel PHB resins respectively, each comprising a polystyrene bead and the cleavable linking arm depicted therein both of which are cleaved by strong acidic conditions such as trifluoroacetic acid. Cleavage results in breakage at the vertical line interposed between the oxygen and carbonyl moieties of the ester so as to provide for a compound terminating in a carboxylic acid.

Figure 2D:
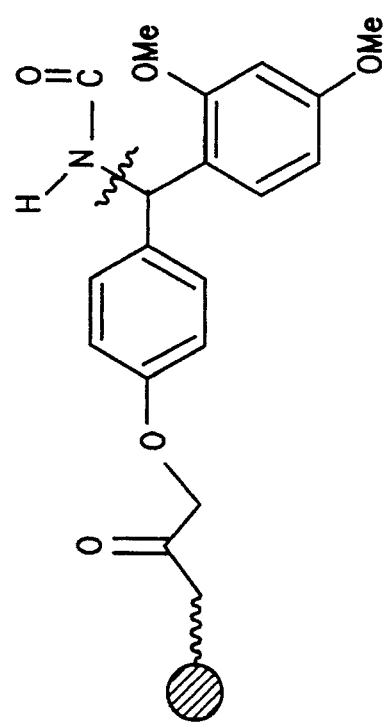

FIG. 2D illustrates a cleavable TentaGel RAM resin comprising a polystyrene bead and a cleavable linking arm depicted therein which is cleaved by strong acidic conditions such as trifluoroacetic acid. Cleavage results in breakage at the vertical line interposed between the nitrogen and the benzhydryl carbon of the linking arm so as to provide for a compound terminating in an amide group. In this case, this linking arm facilitates formation of the amide bond by stabilizing the intermediate carbonium ion on the carbon atom between the two aromatic groups. Such stabilization permits selective bond cleavage as compared to bond cleavage for other amide groups of the compound comprising a pyrrolidinyl group.

"Non-cleavable linking arms" refer to linking arms wherein one or more of the covalent bonds linking the compound comprising a pyrrolidinyl linking group to the solid support can only be cleaved under conditions which chemically alters unintended parts of the structure of the compound attached thereto.

The term "pyrrolidinyl group" refers to a saturated 5-member ring heterocyclic compound containing one (1) ring nitrogen atom optionally containing vinyl unsaturation between carbons 3 and 4 of the ring. When fully saturated, the pyrrolidinyl group can be depicted as follows:

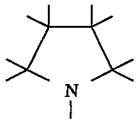

Substituents to the pyrrolidinyl group can occur at any of the ring atoms including the nitrogen atom in the manner depicted above. Such substituents are governed solely by the reagents employed thereby providing flexibility in preparing a large library of pyrrolidinyl compounds. Suitable substituents include, by way of example only:

alkyl groups of from 1 to 10 carbon atoms optionally substituted with 1 or more (typically up to 5) substituents selected from the group consisting of hydroxyl, halo, cyano, amino, mono- and di-alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —NR$^1$C(O)R$^2$ where R$^1$ and R$^2$ are independently selected from the group consisting of hydrogen and alkyl of from 1 to 10 carbon atoms, heterocycles having from 2 to 6 carbon atoms and 1 to 3 ring hetero atoms selected from the group consisting of nitrogen, oxygen and sulfur, aryl groups of from 6 to 10 carbon atoms optionally substituted with from 1 to 3 substituents on the aryl moiety selected from the group consisting of halo, hydroxyl, amino, cyano, carboxyl, nitro, alkyl of from 1 to 10 carbon atoms, alkoxyl of from 1 to 10 carbon atoms, alkoxy of from 1 to 10 carbon atoms optionally substituted with 1 or more (typically up to 5) substituents selected from the group consisting of hydroxyl, halo, cyano, amino, mono- and di-alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —NR$^1$C(O)R$^2$ where R$^1$ and R$^2$ are independently selected from the group consisting of hydrogen and alkyl of from 1 to 10 carbon atoms, heterocycles having from 2 to 6 carbon atoms and 1 to 3 ring hetero atoms selected from the group consisting of nitrogen, oxygen and sulfur, aryl groups of from 6 to 10 carbon atoms optionally substituted with from 1 to 3 substituents on the aryl moiety selected from the group consisting of halo, hydroxyl, amino, cyano, carboxyl, nitro, alkyl of from 1 to 10 carbon atoms, alkoxyl of from 1 to 10 carbon atoms, carboxyl groups, carboxyl ester groups wherein the ester group comprises from 1 to 10 carbon atoms, R—C(O)— groups where R is alkyl of from 1 to 10 carbon atoms optionally substituted on the alkyl group with 1 or more (typically up to 5) substituents selected from the group consisting of hydroxyl, halo, cyano, amino, mono- and di-alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —NR$^1$C(O)R$^2$ where R$^1$ and R$^2$ are independently selected from the group consisting of hydrogen and alkyl of from 1 to 10 carbon atoms, heterocycles having from 2 to 6 carbon atoms and 1 to 3 ring hetero atoms selected from the group consisting of nitrogen, oxygen and sulfur, aryl groups of from 6 to 10 carbon atoms optionally substituted with from 1 to 3 substituents on the aryl moiety selected from the group consisting of halo, hydroxyl, amino, cyano, carboxyl, nitro, alkyl of from 1 to 10 carbon atoms, alkoxyl of from 1 to 10 carbon atoms, aryl groups of from 6 to 10 carbon atoms optionally from 1 to 3 substituents on the aryl moiety selected from the group consisting of halo, hydroxyl, amino, cyano, carboxyl, nitro, alkyl of from 1 to 10 carbon atoms, alkoxyl of from 1 to 10 carbon atoms.

In one embodiment, the pyrrolidinyl group contains a carboxyl substituent alpha to the nitrogen ring atom to provide for proline derivatives. It being understood that such proline derivatives are a preferred subclass of the herein described pyrrolidinyl groups.

In another embodiment, the methods described herein permit the incorporation of unsaturation between carbon atoms 3 and 4 of the pyrrolidinyl group. While inclusion of such unsaturation alters the nomenclature of the resulting compounds to 3-pyrrolinyl, they are nevertheless encompassed within the scope of the term "pyrrolidinyl" for the purposes of this disclosure. When the ring contains such unsaturatation, the pyrrolidinyl group can be depicted as follows:

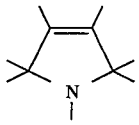

The term "a compound having at least one imine group with a methine or methylene hydrogen atom α to the nitrogen atom of the imine group" refers to any compound which structure comprises a

>C=N—CHR— group covalently attached to the compound wherein R is any substituent which does not form an unsaturated moiety with the CH group so that the CHR group defines a methine or methylene group.

The term "a complementary compound (group or moiety) having at least one site of carbon-carbon unsaturation" refers to those compounds, groups and moieties having carbon-carbon unsaturation which are reactive with azomethine ylides to form pyrrolidinyl compounds. Such complementary compounds, groups and moieties preferably employ an activating group to facilitate reaction with the azomethine ylide and one group of preferred activating groups is an electron withdrawing substituent or group which is preferably covalently attached to at least one of the unsaturated carbon atoms of the complementary compound, group or moieties. Suitable complementary compounds having at least one site of carbon-carbon unsaturation which contain an electron withdrawing group include, by way of example only, acrylic acid, acrolein, methacrylic acid, α-cyanoacrylic acid, acrylonitrile, fumaric acid, maleic acid, maleic anhydride, maleimide, N-substituted maleimide, acrylonitrile, acetylene dicarboxylic acid, isocrotonoic acid, crotononitrile, as well as esters of any of the recited carboxylic acids, and the like. Particular preferred complementary compounds having at least one site of carbon-carbon unsaturation include, by way of example, dimethyl maleate, dimethyl fumurate, methyl acrylate, methyl methacyrlate, phenyl acrylate, ethyl acrylate, and acrylonitrile.

Preferred complementary groups or moieties having at least one site of carbon-carbon unsaturation include those derived from the compounds recited above but which are covalently attached to a larger molecule, e.g., a —CH=CH—CN group, etc.

As noted above, the carbon-carbon unsaturation includes both ethylenic unsaturation (i.e., >C=C<) and acetylenic unsaturation (i.e., —C≡C—). Use of a complementary compound, group or moiety having ethylenic unsaturation results in a saturated pyrrolidinyl group whereas the use of a complementary compound, group or moiety having acetylenic unsaturated results in a pyrrolidinyl compound having ethylenic unsaturation between carbon atoms 3 and 4 of the pyrrolidinyl group (i.e., a pyrrolinyl group).

The particular complementary compound having carbon-carbon unsaturation employed in the methods described herein is not critical.

Methods for Preparing Pyrrolidinyl Groups on Solid Supports

The synthesis of a pyrrolidinyl group on the solid support is effected by reaction of an azomethine ylide with a complementary compound having carbon-carbon unsaturation. In turn, an azomethine ylide is generated from an azomethine ylide precursor compound by methods well known in the art. Surprisingly, it has been found that these known methods can be conducted on solid supports thereby providing methods for generating libraries of compounds containing pyrrolidinyl groups on solid supports.

Figure 1:
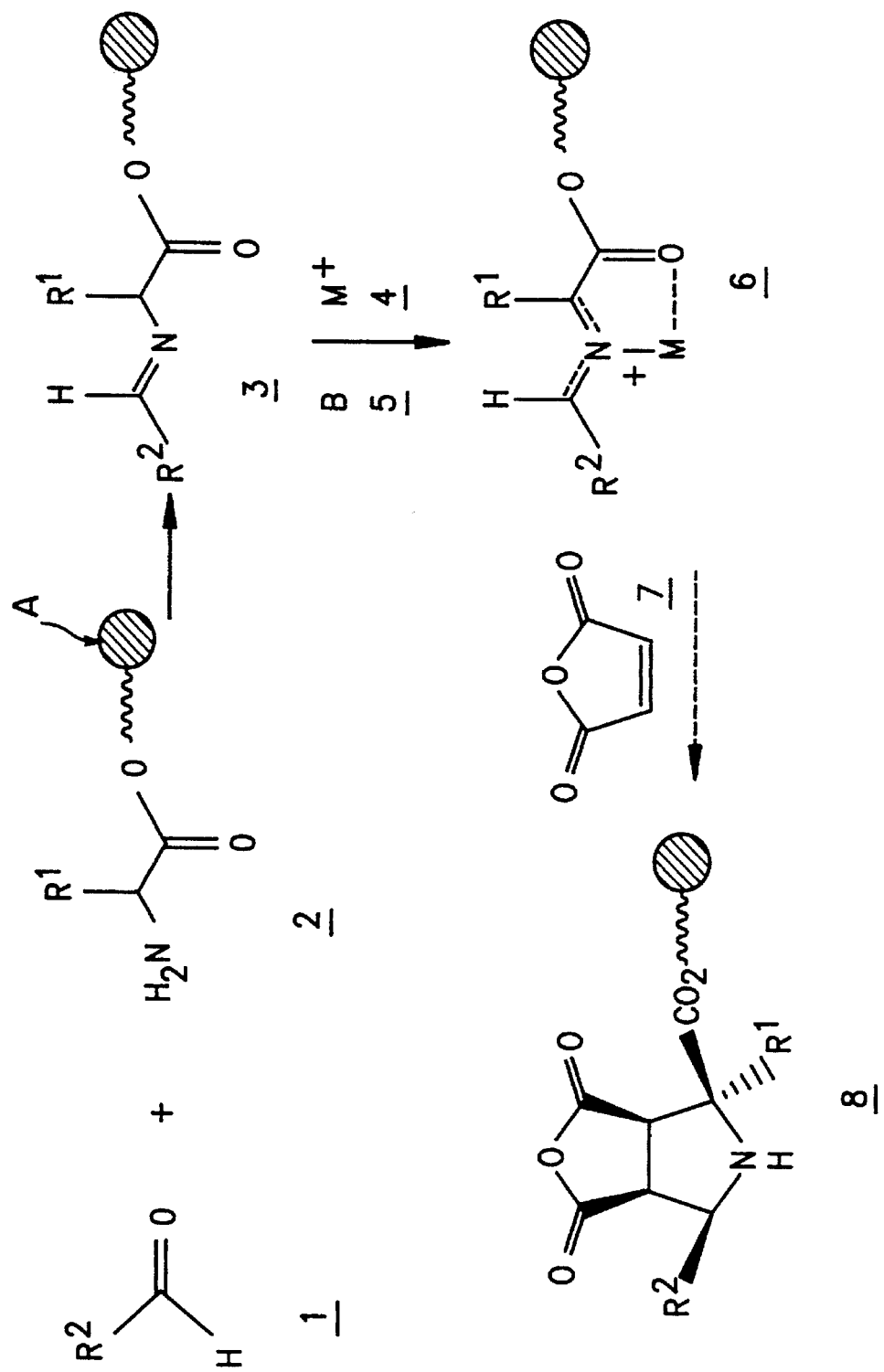
FIG. 1 illustrates the synthesis of an azomethine ylide precursor 3 on a solid support A, conversion of precursor 3 to azomethine ylide 6 and subsequent formation of pyrrolidinyl group 8.

The generation of an azomethine ylide from a precursor molecule is well documented in the art.[14-31] However, one particularly preferred method is the treatment of an imine having a methine or methylene hydrogen atom alpha to the nitrogen atom of the imine group with a base (B) of sufficient basicity to extract this methine or methylene hydrogen atom. Specifically, as illustrated in FIG. 1, imine 3 is treated with base 5 to provide for azomethine ylide 6. The resulting azomethine ylide 6 is reacted with a complementary compound having carbon-carbon unsaturation which, in FIG. 1, is illustrated with maleic anhydride 7 to provide for pyrrolidinyl compound 8.

Each procedure (formation of the azomethine ylide and reaction of this ylide with the complementary compound having carbon-carbon unsaturation) for this reaction is preferably conducted in a single reaction medium. The first procedure for this reaction is conducted in an inert solvent with a stoichiometric or excess amount of base 5 relative to imine 3. The particular solvent employed is not critical and suitable solvents include, by way of example only, acetonitrile, dimethylformamide, tetrahydrofuran and the like. Likewise, the particular base employed is not critical and is selected relative only to its ability to extract the methine or methylene hydrogen atom thereby generating the azomethine ylide. Suitable bases include, by way of example only, triethylamine, diazabicyclo[4.3.0]un-decene, pyridine, diazabicyclo[2.2.2]octane, η-butyllithium, lithium diisopropylamine, and the like.

The reaction is optionally, but preferably, conducted in the presence of at least an approximate stoichiometric amount of a lewis acid 4 which facilitates reaction completion by enhancing the acidity of the methine or methylene hydrogen atom. Additionally, when a carbonyl group is β to the nitrogen atom of the imine (as depicted in compounds 3 and 6 of FIG. 1), the metallic cation of the lewis acid chelates with this carbonyl group thereby increasing the acidity of the methine or methylene hydrogen interposed between the nitrogen atom of the imine and the carbon atom of the carbonyl group. In turn, this increase in acidity permits the use of milder bases to effect extraction of the methine or methylene hydrogen atom.

Suitable lewis acids are well known in the art and the particular lewis acid employed is not critical. In one preferred embodiment, the lewis acid is selected from the group consisting of silver(I) nitrate, silver(I) carbonate, lithium chloride, lithium bromide, and the like which are depicted as $M^+$ in FIG. 1.

The complementary compound having carbon-carbon unsaturation is preferably added to this reaction medium prior to initiation of the reaction so that upon formation, the azomethine ylide is in situ converted to pyrrolidinyl compound 8.

The reaction conditions are otherwise not critical and, preferably, the reaction is conducted at from about 0° C. to about 100° C. for from about 0.5 to about 24 hours.

The resulting pyrrolidinyl compound 8 is recovered by conventional methods, i.e., filtration, centrifugation, etc. Confirmation that the resin (i.e., solid support) contains the desired pyrrolidinyl compound can be accomplished by cleaving the pyrrolidinyl compound from a small portion of the treated resins (if a cleavable linking arm is employed) and subjecting this product to conventional analysis, e.g., nuclear magnetic resonance spectroscopy ($^1H$, $^{13}C$, etc.), high performance liquid chromatography, and the like. Alternatively, the reaction can be monitored by use of appropriate resins using gel-phase $C^{13}$-nuclear magnetic resonance spectroscopy. Suitable resins for this use include those illustrated in FIGS. 2B–2D attached.

Other means for forming azomethine ylides from suitable azomethine ylide precursors are well known in the art and include by way of example, ring opening of aziridines[1]. The particular azomethine ylide precursor employed and the method employed to convert this precursor to the azomethine ylide is not critical. For example, suitable azomethine ylide precursors can employ a silyl group as disclosed by Tsuge, et al.[1] which can be converted to the azomethine ylide without the need for a base. Such precursors are of particular value when basic conditions are to be avoided.

FIG. 1 further illustrates the formation of imine compound 3, which serves as an azomethine ylide precursor, by conventional methods from a suitable aldehyde 1 (ketones can also be used) and amine 2. The reaction is conducted in an inert solvent under conditions which eliminate water thereby forming imine 3. Preferred inert solvents include those that will form an azeotrope with water so that water generated during reaction can be readily removed. Such preferred solvents include by way of example, benzene, toluene, etc. Particularly preferred reaction conditions include the use benzene or benzene/triethylamine under refluxing conditions; the use of benzene/Dean Stark trap or 4A molecular sieves under refluxing conditions; the use of methanol or methanol/triethylamine; the use of tetrahydrofuran/$Si(OC_2H_5)_4$/1% $H_2SO_4$; and the use of trimethyl orthoformate.

FIG. 1 illustrates formation of imine 3 from amine 2 attached to a solid support which is reacted with soluble aldehyde 1. It is understood, however, that aldehyde 1 (or a ketone) can be covalently attached to the solid support and that amine 2 is in soluble form (i.e., not attached to the solid support). In both cases, the resulting imine is covalently bound to the solid support.

It is further understood, however, that the complementary compound having at least one site of carbon-carbon unsaturation can be covalently attached to the solid support which can then be reacted with a soluble azomethine ylide (not attached to the support) to provide for a pyrrolidinyl group covalently attached to the support. In such an embodiments, this reaction is conducted in the manner to that described above.

In the particular embodiment illustrated in FIG. 1, the amine 2 is an amino acid wherein the acid group is attached to the solid support via an ester bond. Such amino acids form a preferred subclass of suitable amines because these amino acids will result in a carbonyl group β to the resulting imine nitrogen. Suitable amino acids include all naturally occurring as well as synthetic amino acids including, by way of example, the D-amino acids of naturally occurring L-amino acids. The amino acid can be the N-terminal amino acid of a peptide bound to the solid support which, after formation of the pyrrolidinyl group can optionally be further reacted under conventional peptide synthetic conditions through an N—H group of the pyrrolidinyl group to extend the peptide length.

Alternatively, the >NH group of the pyrrolidinyl compound can be acylated via conventional means to provide for acylated pyrrolidinyl compounds. A particularly preferred class of acylating reagents include those of the formula $HSCH_2CHR^3C(O)$— which, when reacted with the pyrrolidinyl compound form a class of Captopril™ derivatives which are then screened for anti-hypertensive activity. $R^3$ being a substituent having the same values as recited above for the substituents listed for the pyrrolidinyl group.

In another embodiment, the aldehyde 1 (or ketone) can comprise ethylenic unsaturation so that the resulting imine can undergo internal cyclization via the ethylenic unsaturation on the aldehyde. Suitable examples of such aldehydes include those of formula I below:

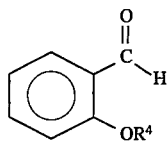

where $R^4$ is —$(CH_2)_n$—CH=$CH_2$ (n=1 or 2), —$CH_2$—CH=CH—$CO_2$ $CH_3$, and —$CH_2$C≡CH.

Method for Producing Large Synthetic Libraries of Pyrrolidinyl Compounds

The above described synthetic methods can be incorporated into one or more reaction procedures in the stochastic methods described in International Patent Application Publication No. 93/06121 to prepare synthetic libraries of pyrrolidinyl compounds on solid supports. This application is incorporated herein by reference in its entirety. In such libraries, each solid support will preferably contain a single compound which compound is different to the compounds found on the other solid supports but each compound will also comprise a pyrrolidinyl compound.

It is understood, however, that the term "single compound" as used herein includes different regio and stereo isomers of that compound. Also, the term "single compound" does not mean that only one copy of that compound is attached to each support. Rather, multiple copies of that compound can be included on the support.

In general, such methods comprise apportioning the supports comprising a covalently bound azomethine ylide precursor or a complementary compound having at least one site of carbon-carbon unsaturation among a plurality of reaction vessels; exposing the supports in each reaction vessel under conditions wherein the azomethine ylide precursor or the complementary compound is converted to a pyrrolidinyl group wherein said pyrrolidinyl group is different for each of the reaction vessels; and pooling the supports.

In one embodiment, the azomethine ylide precursor is converted to a pyrrolidinyl group by first converting the ylide precursor to an azomethine ylide followed by reaction of the azomethine ylide with a complementary compound having at least one site of carbon-carbon unsaturation.

In another embodiment, the complementary group containing at least one site of carbon-carbon unsaturation is converted to a pyrrolidinyl group by reaction with an azomethine ylide.

In a preferred aspect of this embodiment, each solid support is tagged with an identifier tag that can be easily decoded to report the compounds formed on the solid support. The tag can be directly attached either to the solid support or the tag can be included on the compound itself. In this latter embodiment, cleavage of the compound from the solid support will still permit identification of the compound. Each of these embodiments is disclosed in International Patent Application Publication No. WO 93/06121. Alternatively, a portion of the same compounds attached to a single support is cleaved and subjected to mass spectroscopy, nuclear magnetic resonance spectroscopy and/or other forms of direct structural analysis so as to identify the compound on the support.

Still another method for incorporating a tag with the solid support is disclosed in U.S. patent application Ser. No. 08/146,886, filed Nov. 2, 1994, and entitled "METHOD OF SYNTHESIZING DIVERSE COLLECTIONS OF COMPOUNDS" which application is incorporated herein by reference in its entirety.

In still another embodiment, the pyrrolidinyl group can be incorporated into each compound in a library of different compounds all of which are covalently linked to the same solid support in the manner described in U.S. Pat. No. 5,143,854. Such a library of different compounds can be simultaneously screened for receptor binding or some other activity. U.S. Pat. No. 5,143,854 is incorporated herein by reference in its entirety.

Additionally, libraries of compounds attached to solid supports can be used for a variety of additional uses as set forth in International Patent Application Publication No. WO 93/06121.

EXAMPLES

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:
app d=apparent doublet
app q=apparent quartet
app t=apparent triplet
Ar=phenyl
br s=broad singlet
d=doublet
dd=doublet of doublets
DMSO-d$_6$=deutrated dimethyl sulfoxide
FMOC=fluorenylmethyl oxycarbonyl
$^1$H-nmr=proton nuclear magnetic resonance
HPLC=high performance liquid chromatography
m=multiplet
MHz=megahertz
mL=milliliter
mmol=millimol
s=singlet
TFA=trifluoroacetic acid Additionally the Sasrin resin described herein is commercially available from Bachem Biosciences and the TentaGel Ac resin, TentaGel PHB resin and TentaGel RAM resin are commercially available from Rapp Polymere, Tubigen, Germany. Each of these resins is depicted in FIGS. 2A–2D respectively.

EXPERIMENTAL

The following experimental outlines the general procedures employed in the examples below to prepare the pyrrolidine compounds depicted therein.

General Solid Phase Condition for Imine Formation

Resin bound glycine FMOC (0.25 mmol loading) is added to 10 mL of 20% piperidine in dimethyl formamide for one hour. The resin is filtered through a fritted funnel and washed with dimethyl formamide (3×10 mL) and methylene chloride (3×20 mL). To a 10 mL round bottom flask is added aldehyde (2.5 mmol) and the resin (0.25 mmol loading) in 8 mL of benzene. The solution is fitted with a Dean Stark trap and filled with benzene and subsequently refluxed mildly for one hour to two hours. The solution is filtered through a fritted glass filter and the residue is washed with benzene (3×10 mL) and methylene chloride (3×10 mL).

General Solid Phase Condition for [2+3] cycloaddition with Silver(I)

To a 10 mL screw capped vial is added resin (0.125 mmol loading), olefin (1.5 mmol), and silver(I) nitrate (1.5 mmol) in approximately 5 mL of acetonitrile. To the solution is added triethyl amine (1.5 mmol) by syringe dropwise in a hood with the light off. The vial is very mildly agitated by a shaker table and the heterogeneous solution is observed to change colors from clear to black in two to four hours and a silver mirror is seen to be present after 8 to 12 hours. After 24 hours the resin solution is filtered through a fritted glass filter and washed with methylene chloride (5×10 mL). The resin is then added to a vial with 4 mL of trifluoroacetic acid in methylene chloride (% TFA varies according to the type of linker employed) for 30 minutes and subsequently filtered and washed with methylene chloride (3×5 mL). This procedure is repeated three times and the filtrates collected and rotary evaporated to dryness. The residue oil is analyzed by $H^1$ NMR and HPLC.

General Solid Phase Condition for [2+3] cycloaddition with Lithium(I)

To a 10 mL screw capped vial is added resin (0.125 mmol loading), olefin (1.5 mmol), and lithium(I) bromide (1.5 mmol) in approximately 5 mL of acetonitrile. To the solution is added triethyl amine (1.5 mmol) by syringe dropwise in a hood with the light off. The vial is agitated very mildly by a shaker table and the heterogeneous solution is observed to change colors from clear to cloudy in two to four hours. After 48 hours the resin solution is filtered through a fritted glass filter and the residue washed with methylene chloride (5×10 mL). The resin is then added to a vial with 4 mL of trifluoroacetic acid in methylene chloride (% TFA varies according to the type of linker employed) for 30 minutes and subsequently filtered and washed with methylene chloride (3×5 mL). This procedure is repeated three times and the filtrates collected and rotary evaporated to dryness. The residue oil is analyzed by $H^1$ NMR and HPLC.

Example 1

By following the procedures set forth above, 4-cyano-5-phenyl-L-proline was prepared as shown below:

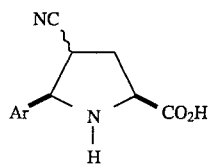

The aldehyde employed in this synthesis was benzaldehyde and the olefin was acrylonitrile. The support employed in this synthesis was Sasrin resin containing the cleavable linker depicted in FIG. 2A which, upon treatment with 25% trifluoroacetic acid (in methylene chloride), gave the soluble proline derivative. $^1$H-nmr data for this compound is as follows: (D$_2$O, 300 MHz) δ7.70–7.41 (m, 5H, ArH), 5.24 (d, 1H, ArCH), 5.15 (d, 1H, ArCH, epimer product at the cyano carbon), 4.72–4.63 (m, 1H, CHCO$_2$H), 4.27–4.14 (m, 1H, CHCN), 4.01–3.55 (m, 2H, CHCN, CHCO$_2$H epimer product at the cyano carbon), 3.11–2.84 (m, 2H, CH$_2$CHCO$_2$H including the epimer product), 2.16–2.10 (br s, 1H, NH). Yield 71.4%.

Example 2

By following the procedures set forth above, 4-cyano-5-phenyl-L-proline was prepared as shown below:

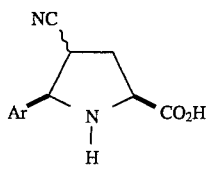

The aldehyde employed in this synthesis was benzaldehyde and the olefin was acrylonitrile. The support employed in this synthesis was TentaGel Ac resin containing the cleavable linker depicted in FIG. 2B which, upon treatment with 25% trifluoroacetic acid in methylene chloride, gave the soluble proline derivative. $^1$H-nmr data for this compound is as follows: $^1$H NMR (DMSO-d$_6$ 300 MHz) δ7.65–7.22 (m, 5H, ArH), 4.94 (app d 1H, ArCH, epimer product at the cyano carbon), 4.92(app d, 1H, ArCH), 4.65 (app t, 1H, CHCO$_2$H, epimer product at the cyano carbon), 4.50 (app t, 1H, C$\underline{H}$CO$_2$H), 4.10 (app q, 1H, C$\underline{H}$CN), 3.81 (app q, 2H, C$\underline{H}$CN, epimer product at the cyano carbon), 3.50 (br s due to glycine), 3.08–2.60 (m, 2H, C$\underline{H}_2$CHCO$_2$H including the epimer product). Yield 40.0% (Ag), 20.7% (Li).

Example 3

By following the procedures set forth above, 4-cyano-5-phenyl-L-proline was prepared as shown below:

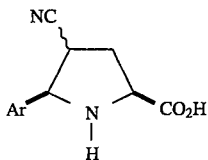

The aldehyde employed in this synthesis was benzaldehyde and the olefin was acrylonitrile. The support employed in this synthesis was TentaGel PHB resin containing the cleavable linker depicted in FIG. 2C which, upon treatment with 95% trifluoroacetic acid in methylene chloride, gave the soluble proline derivative. $^1$H-nmr data for this compound is as follows: $^1$H-nmr (DMSO-d$_6$ 300 MHz) δ7.65–7.38 (m, 5H, Ar$\underline{H}$), 4.89 (app d, 1H, ArC$\underline{H}$), 4.87 (app d, 1H, ArC$\underline{H}$, epimer product at the cyano carbon), 4.65(app t, 1H, C$\underline{H}$CO$_2$H, epimer product at the cyano carbon), 4.48 (app t, 1H, C$\underline{H}$CO$_2$H), 4.15–4.08 (m, 1H, C$\underline{H}$CN), 3.81 (m, 2H, C$\underline{H}$CN, epimer product at the cyano carbon), 3.50 (s due to glycine), 3.01–2.67 (m, 2H, C$\underline{H}_2$CHCO$_2$H including the epimer product), 2.16–2.10 (br s, 1H, N$\underline{H}$). Yield 12.6% (Ag), 8.0% (Li).

Example 4

By following the procedures set forth above, 2-amido-4-cyano-5-phenyl-L-pyrrolidine was prepared as shown below:

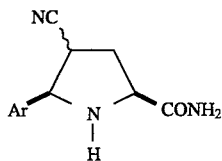

The aldehyde employed in this synthesis was benzaldehyde and the olefin was acrylonitrile. The support employed in this synthesis was TentaGel RAM resin containing the cleavable linker depicted in FIG. 2D which, upon treatment with 95% trifluoroacetic acid in methylene chloride, gave the soluble amide derivative. $^1$H-nmr data for this compound is as follows: (DMSO-d$_6$ 300 MHz) δ8.15 (br s, 2H, CON$\underline{H}_2$), 7.98–7.45 (m, 5H,Ar$\underline{H}$), 5.02 (dd, 1H, C$\underline{H}$CONH$_2$), 4.80 (d 1H, ArC$\underline{H}$), 4.49(m, 1H, C$\underline{H}$CN), 3.50 (s due to glycine), 2.85–2.40 (m, 2H, C$\underline{H}_2$CHCONH$_2$). Yield 11.1% (Li).

Example 5

By following the procedures set forth above, 4-carboxymethyl-4-methyl-5-phenyl-L-proline was prepared as shown below:

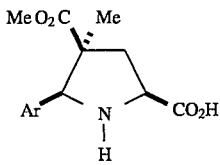

The aldehyde employed in this synthesis was benzaldehyde and the olefin was methyl methacrylate. The support employed in this synthesis was TentaGel AC resin which, upon treatment with 25% trifluoroacetic acid in methylene chloride, gave the soluble proline derivative. $^1$H-nmr data for this compounds is as follows: (DMSO-d$_6$ 300 MHz) δ7.47–7.20 (m, 5H, Ar$\underline{H}$), 4.79 (dd, 1H, C$\underline{H}$CO$_2$H), 4.73 (d 1H, ArC$\underline{H}$), 3.65 (s due to glycine), 3.49 (s, 3H, CO$_2$C$\underline{H}_3$), 3.24–3.16 (m, 1H, N$\underline{H}$) 2.86 (dd, 1H, C$\underline{H}_2$CHCO$_2$H), 2.60 (dd, 1H, C$\underline{H}_2$CHCO$_2$H), 1.43 (s,3H,C$\underline{H}_3$). The regiochemistry of this compound is unclear. Yield 46.4% (Ag), 30.4% (Li).

Example 6

By following the procedures set forth above, 4-carboxymethyl-4-methyl-5-phenyl-L-proline was prepared as shown below:

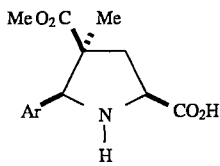

The aldehyde employed in this synthesis was benzaldehyde and the olefin was methyl methacrylate. The support employed in this synthesis was TentaGel PBH resin which, upon treatment with 95% trifluoroacetic acid in methylene chloride, gave the soluble proline derivative. $^1$H-nmr data for this compounds is as follows: (DMSO-d$_6$ 300 MHz) δ7.47–7.20 (m, 5H, Ar$\underline{H}$), 4.79 (dd, 1H, C$\underline{H}$CO$_2$H), 4.73 (d 1H, ArC$\underline{H}$), 3.65 (s due to glycine), 3.49 (s, 3H, CO$_2$C$\underline{H}_3$), 3.24–3.16 (m, 1H, N$\underline{H}$), 2.86 (dd, 1H, C$\underline{H}_2$CHCO$_2$H), 2.60 (dd, H,C$\underline{H}_2$CHCO$_2$H), 1.43 (s, 3H, C$\underline{H}_3$). The regiochemistry of this product is unclear. Yield 17.1% (Ag), 38.6% (Li).

Example 7

By following the procedures set forth above, 2-amido-4-carboxymethyl-4-methyl-5-phenyl-L-pyrrolidine was prepared as shown below:

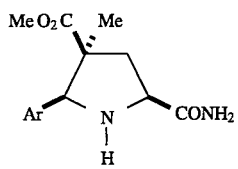

The aldehyde employed in this synthesis was benzaldehyde and the olefin was methyl methacrylate. The support employed in this synthesis was TentaGel RAM resin which, upon treatment with 95% trifluoroacetic acid in methylene chloride, gave the soluble amide derivative. $^1$H-nmr data for this compounds is as follows: (DMSO-$d_6$ 300 MHz) δ7.48–7.20 (m, 5H, ArH), 6.50 (br s, 2H, CONH$_2$), 5.10 (dd, 1H, CHCONH$_2$), 4.70 (s 1H,ArCH), 3.65 (s due to glycine), 3.49 (s, 3H, CO$_2$CH$_3$), 3.24–3.16 (m, 1H, NH), 2.86 (dd, 1H, CH$_2$CHCONH$_2$), 2.62 (dd, 1H, CH$_2$CHCONH$_2$), 1.50 (s, 3H, CH$_3$). The regiochemistry of this product is unclear. Yield 32.3% (Ag), less than 4.8% (Li).

By following the procedures set forth above, other amino acids can be employed in place of glycine on the solid supports or peptides of up to about 20 amino acids could be employed merely by substitution of such materials for the glycine/solid support materials described in these examples. Moreover, after completion of the synthesis of the pyrrolidine compound, the amino —NH group of this compound can be acylated using conventional chemistry, including acylation resulting in the incorporation of one or more amino acids thereto.

Likewise, other aldehydes or ketones could be employed in place of the benzaldehyde to provide different substitution at the 5 position of the resulting pyrrolidine compounds.

What is claimed is:

1. A method for synthesizing a pyrrolidinyl group covalently attached to a solid support which method comprises:

(a) selecting a solid support comprising at least one compound covalently attached thereto which compound comprises a moiety selected from the group consisting of a complementary group having at least one site of carbon-carbon unsaturation and an azomethine ylide precursor;

(b) converting said moiety to a pyrrolidinyl group.

2. The method according to claim 1 wherein said moiety is an azomethine ylide precursor which is converted to a pyrrolidinyl group by first converting this precursor to an azomethine ylide followed by reaction with a complementary compound having at least one site of carbon-carbon unsaturation.

3. The method according to claim 1 wherein said moiety is a complementary group having at least one site of carbon-carbon unsaturation which is converted to a pyrrolidinyl group by reaction with an azomethine ylide.

4. The method according to claim 1 wherein the azomethine ylide precursor is an imine group having a methine or methylene hydrogen atom alpha to the nitrogen atom of the imine group or is convertible to such an imine group.

5. The method according to claim 2 wherein the complementary compound having at least one site of carbon-carbon unsaturation is selected from the group consisting of dimethyl maleate, dimethyl fumarate, methyl acrylate, methyl methacrylate, phenyl acrylate, ethyl acrylate, and acrylonitrile.

* * * * *